US00PP15544P3

(12) United States Plant Patent
Corley

(10) Patent No.: US PP15,544 P3
(45) Date of Patent: Feb. 8, 2005

(54) ***RHAPHIOLEPIS* PLANT NAMED 'CORLEYSCOURII'**

(50) Latin Name: *Rhaphiolepis×delacourii*
Varietal Denomination: Corleyscourii

(76) Inventor: Willie Lee Corley, 113 Hummingbird Hollow, Griffin, GA (US) 30223

( * ) Notice: Subject to any disclaimer, the term of this patent is extended or adjusted under 35 U.S.C. 154(b) by 0 days.

(21) Appl. No.: 10/352,337

(22) Filed: Jan. 27, 2003

(65) Prior Publication Data

US 2004/0148672 P1 Jul. 29, 2004

(51) Int. Cl.[7] ..... A01H 5/00

(52) U.S. Cl. ..... Plt./254

(58) Field of Search ..... Plt./254

*Primary Examiner*—Kent Bell

(74) *Attorney, Agent, or Firm*—Klarquist Sparkman, LLP

(57) ABSTRACT

A *Rhaphiolepis×delacourii* plant named 'Corleyscourii' characterized by its resistance to leaf spot, burgundy winter foliage, compact habit, cold hardiness and uniform floriferousness.

6 Drawing Sheets

Latin name of the genus and species of the plant claimed: *Rhaphiolepis×delacourii.*

Variety denomination: 'Corleyscourii'.

BACKGROUND

*Rhaphiolepis×delacourii* 'Corleyscourii' is the result of a cross between *R. umbellata* and *R. indica. Rhaphiolepis umbellata* is a shrub native to Japan and Korea while *R. indica* hails from China. *Rhaphiolepis umbellata* and *R. indica* where first crossed by one Delacour (hence× *delacourii*), in Cannes, France, in the late nineteenth century. *Rhaphiolepis* species are grown chiefly as ornamental flowering and evergreen shrubs for low hedges, groupings, and mass plantings.

The present invention relates to a new and distinct variety of *Rhaphiolepis×delacourii* which is characterized by its resistance to leaf spot disease caused by *Entomosporium* spp., seasonal foliage color, compact habit, cold hardiness, and uniform floriferousness. This variety is the result of efforts to identify and propagate Indian Hawthorn varieties which are aesthetically pleasing and resistant to pathogens which have disfigured plantings of *Rhaphiolepis* throughout the southeastern U.S., in particular leaf spot, *Entomosporium* spp.

All progeny of *Rhaphiolepis×delacourii* 'Corleyscourii' are derived from a single disease-resistant individual original plant which was grown from an open-pollinated seed which was collected from a single *Rhaphiolepis×delacourii* 'Georgia Petite' (U.S. Plant Pat. No. 9,983) growing in Griffin, Ga. Thus 'Corleyscourii' has 'Georgia Petite' as its seed parent and is similar to 'Georgia Petite' in its compact habit, disease resistance, and cold hardiness. The new variety differs from 'Georgia Petite' in that the dark green evergreen foliage of the new variety provides exceptional winter interest by turning a beautiful rich burgundy.

BRIEF SUMMARY

*Rhaphiolepis×delacourii* 'Corleyscourii' has been asexually propagated at a location near Athens, Ga. by softwood cuttings. The observations below, unless otherwise indicated, are from asexually propagated progeny growing in Monroe, Ga. Observations of my new variety have confirmed that the following unique combination of characteristics remain fixed in succeeding generations and distinguish *Rhaphiolepis×delacourii* 'Corleyscourii'.

1. Leaf spot- and fire blight-resistant foliage (resistant to *Entomosporium* spp.).
2. Evergreen leaves that offer highly ornamental, uniform, burgundy winter leaf coloration. The richness of the burgundy color is a desirable feature in the winter landscape.
3. Cold hardiness and heat tolerance.
4. Growth that has proven to be exceptionally tight and compact, with dense foliage.
5. Uniform flowering throughout the expanse of the plant. 'Corleyscourii' has not been observed to become leggy and tight branching occurs even at the base of the plant, thus creating uniform flowering over the entire canopy.

BRIEF DESCRIPTION OF THE DRAWINGS

The accompanying photographs depict the color of the plant, flowers and foliage of my new variety as nearly as is reasonably possible to make the same in a color illustration of this character. It should be noted that colors in a photograph can vary with lighting conditions. Also, growing conditions can affect plant color.

DETAILED BOTANICAL DESCRIPTION

Figure 1:
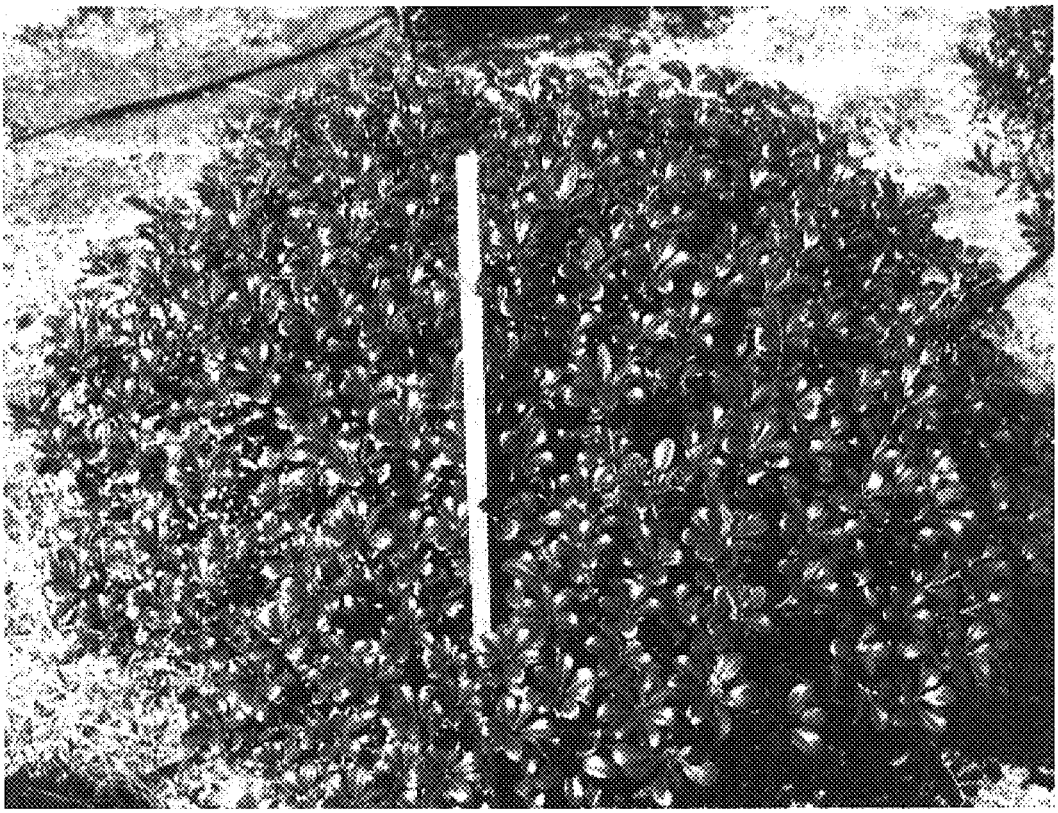
FIG. 1. The new variety in its winter leaf coloration: The dark green of the summer leaves has become an attractive rich dark burgundy.
Figure 2:
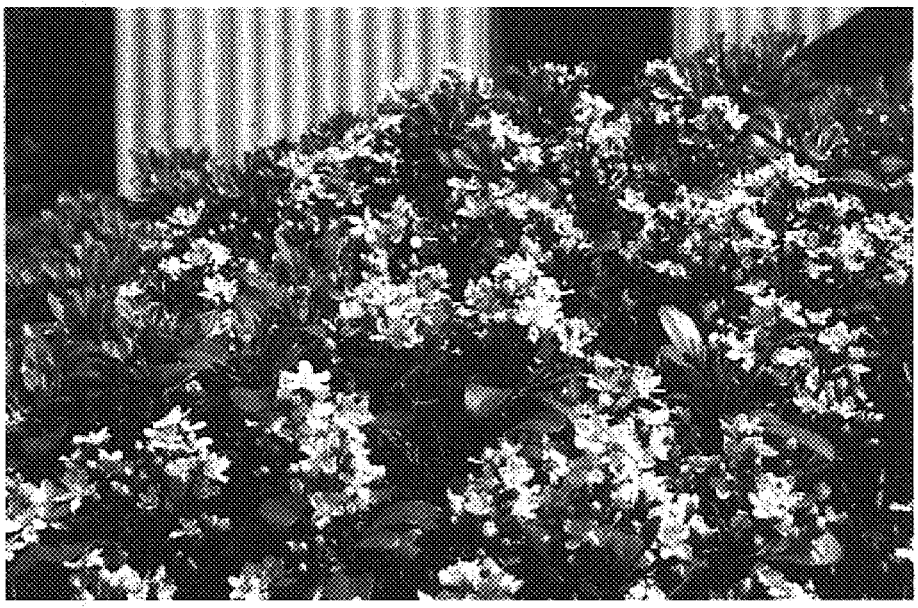
FIG. 2. The new variety when flowering. The plant is a small rounded shrub covered in white flowers. The mound exhibits tight branching from the base to the top (no legginess), and displays a mantle of flowers from the ground up.
Figure 3:
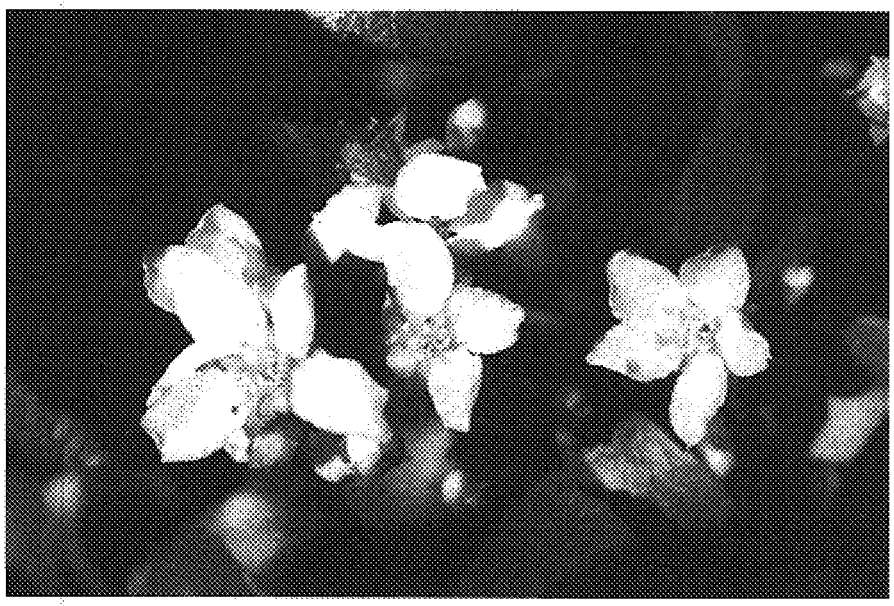
FIG. 3. Flowers of the new variety.
Figure 4:
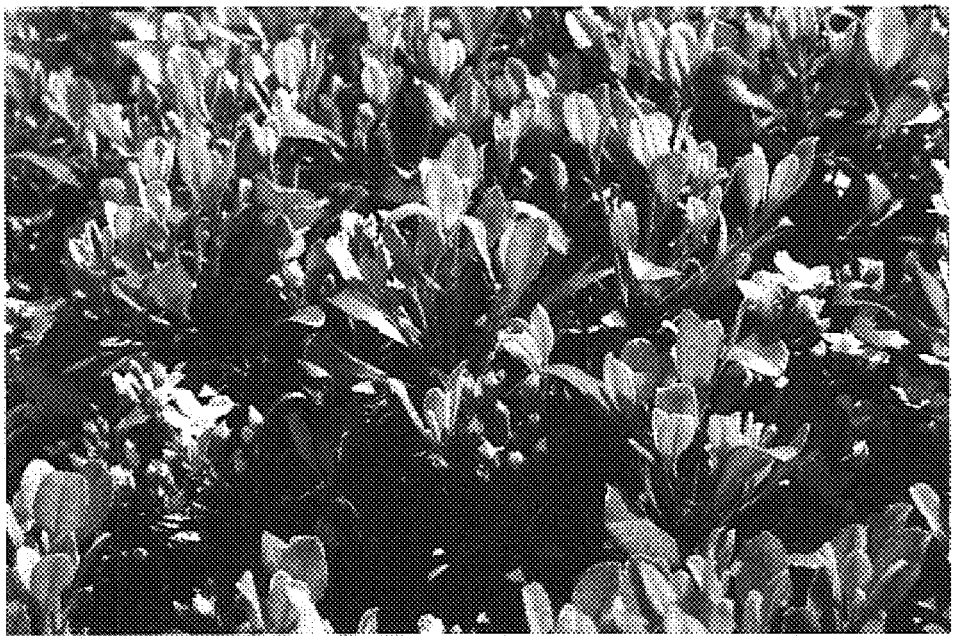
FIG. 4. Close up of a portion of the plant of the new variety.
Figure 5:
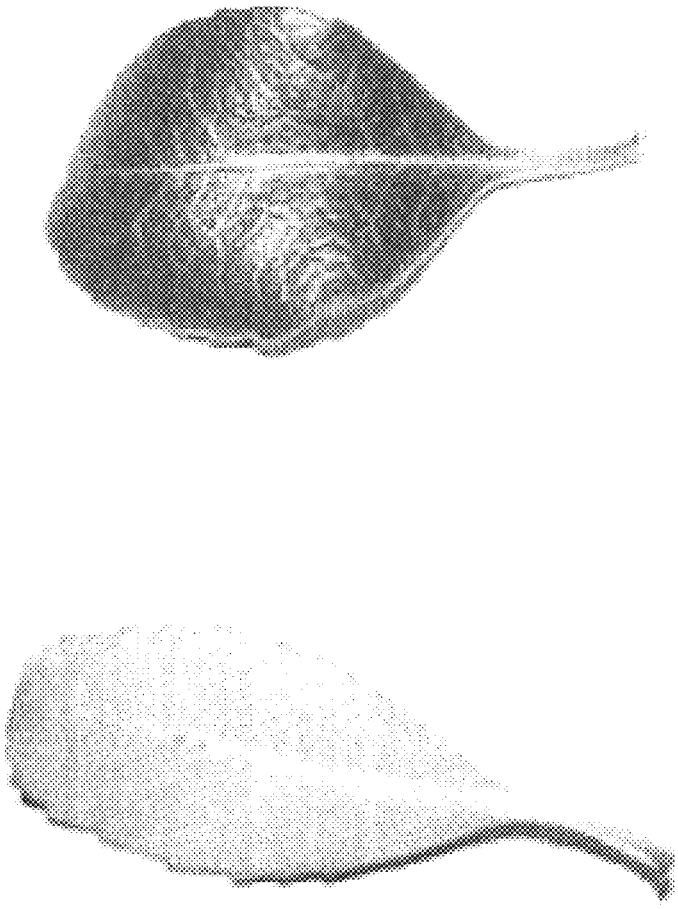
FIG. 5. Top and bottom views of summer leaves from the new variety.
Figure 6:
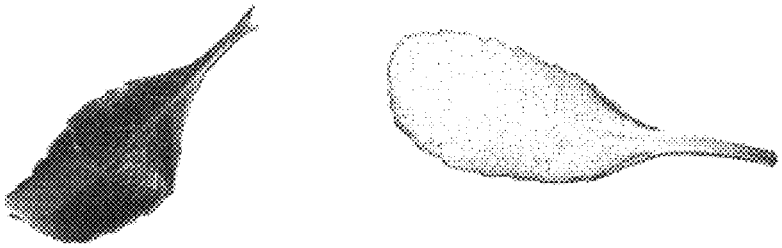
FIG. 6. Top and bottom views of winter leaves from the new variety.

The following is a botanical description of *Rhaphiolepis×delacourii* 'Corleyscourii' based on four year old specimens (unless otherwise noted) grown in the field at Monroe, Ga. with color references pursuant to The Royal Horticultural Society Colour Chart (R.H.S.).

Scientific name: *Rhaphiolepis×delacourii,* Varietal Name 'Corleyscourii'.

Parentage:

*Seed parent.*—*Rhaphiolepis×delacourii* 'Georgia Petite'.

*Pollen parent.*—Unknown.

Propagation: 'Corleyscourii' is easily reproduced, true to type, from softwood cuttings. Tip cuttings are taken when the first flush of growth hardens (June in Monroe, Ga.). Cuttings are dipped for 3 to 5 seconds in 5000 ppm KIBA. Cuttings are stuck under mist in a lightweight media and usually root at a rate of 75% or better in 6 to 8 weeks.

Habit:

*Habit.*—Low, rounded, tight, and dense, with multiple shoots arising in the spring from vegetative buds formed the previous season around the terminus of the branch. Average number of breaks is 10.7 (range from 6 to 18 new shoots). Internodes are short, averaging 1 cm, resulting in the tight form.

*Rate.*—Vigorous when young, but slows with age resulting in an average growth rate of 20 cm per year. The observed plant was only 66 cm high and 102 cm wide after 4 years (average of 6 plants) and 80 cm high and 145 cm wide after 6 years (average of 10 plants).

Leaves: Evergreen, simple, arranged alternately with internodes spacing averaging 1 cm. Leaves are arranged mostly around the tip of the new growth creating an effect that almost looks whorled.

*Shape.*—Obovate to elliptic.

*Margin.*—Serrate, undulate, those on the outside of canopy with a burgundy margin in summer (RHS greyed-purple group 187A).

*Base.*—Cuneate.

*Apex.*—Obtuse.

*Surface.*—Leathery, thick, glabrous at maturity, 7 to 8 vein pairs.

*Length and width.*—5.72 cm long and 2.54 cm wide.

*Color.*—Summer leaves: Upper surface: Flat dark green (RHS yellow-green group 147A). Lower surface: Flat pale green (RHS yellow-green group 147D). Edge Margin: Burgundy (RHS greyed-purple group 187A) for upper and lower edge margins of leaves on outside of canopy. Winter leaves: Upper surface (including edge margin): Burgundy (RHS greyed-purple group 187A). Lower surface: RHS Greyed-Purple Group 187C with edge margin RHS greyed-purple group 187A. New leaves: Upper surface: Medium green (RHS yellow-green group 146C) with beige (RHS greyed-orange group 165C) tomentum. Lower surface: RHS Yellow-Green Group 146D with edge margin RHS greyed-purple group 187C.

*Petiole.*—1.27 cm long, flat, glabrous. Summer: RHS Yellow-Green Group 145B. Winter: RHS Greyed-Purple Group 187C. New: RHS Yellow-Green Group 146C.

*Buds.*—Terminal buds: produce flowers and vegetative growth in the spring from buds that are solitary, conical, scales imbricate, 3 scales, 1/16 inches high and wide, light green (RHS yellow-green group 145B) and produce vegetative growth again in mid-summer from buds that are solitary, conical, scales imbricate, 1/16 inches high and wide, light brown (RHS grey-brown group 199D) with white (RHS white group 155D) pubescence. Lateral buds: ensconced in the bark; buds observed as of this time to only break into growth when terminal is pruned.

Stems:

*Surface.*—1st year — bright green (RHS yellow-green group 144C) with beige (RHS greyed-orange group 165C) tomentum; 2nd year — flat light brown (RHS grey-brown group 199D) with vertical fissures.

*Pith.*—Solid, uniform, pale green (RHS green group 139D) with pale yellow (RHS yellow-green group 150D) vascular tissue.

*Leaf scar.*—2 mm wide, 1 mm high, crescent-shaped, 3 bundle traces.

*Stem size* (*average of 10 stems*).—After first year of growth: length 20 cm and diameter (2.5 cm from tip) 4 mm. After second year of growth: length 20 cm and diameter (2.5 cm from tip) 5.5 mm.

Flowers:

*Color of petals.*—Upper surface and lower surface: White (RHS white group 155D) with rose (RHS red-purple group 65D) markings.

*Size.*—1.91 cm diameter flowers; each petal 9.53 mm long, 6.35 mm wide.

*Botanical description.*—Rosaceous flower with 5 petals, 5 sepals, 15 stamens, 3 styles to 1 ovary. Stamens with white (RHS white group 155D) filament and yellow (RHS yellow group 3D) anthers. After anthesis filament turns pink (RHS red-purple group 62C) then red (RHS red-purple group 59A) and anthers brown (RHS greyed-orange group 165A) and a brown (greyed-orange group 164B) pubescence develops at base of petals.

*Petals.*—The 5 petals are separate (not fused). Shape of petal apex is truncate. Shape of petal base is acute. Margin: entire, wavy. Texture is silky smooth.

*Sepals.*—5 sepals, fused at base to calyx cup. Length: 5 mm. Width: 1.5 mm. Shape is triangular. Shape of sepal apex is acute. Shape of sepal base is truncate, fused to calyx cup. Margin is entire. Texture is tomentose. Color: RHS yellow-green group 145A with beige (RHS greyed-orange group 165C) tomentum.

*Calyx Cup.*—RHS Yellow-Green Group 145A with beige (RHS greyed-orange group 165C) tomentum, 4 mm long, 2.5 mm diameter at top, 1.2 mm diameter at bottom.

*Pistils.*—1 pistil per flower comprising, 3 styles and 1 ovary, ovary superior with petals and stamens perigynous. Color: RHS yellow-green group 150C. Pollen amount: 40 grains per square mm. Pollen color: RHS Yellow-Group 4A.

*Peduncle.*—Length: ½ mm. Diameter: 1.2 mm. Color: RHS yellow-green group 145A with beige (RHS greyed-orange group 165C) tomentum. Pistil, stigma, and style are 8 mm long, ⅓ mm wide, ovary is 1.5 mm long, 1 mm wide.

*Stamens.*—Anther is 6 mm long, ½ mm wide; filament is 1 mm long, ½ mm wide.

*Inflorescence type.*—Panicle, 5.08 to 7.62 cm wide, 5.08 to 7.62 cm high, average of 16 flowers per inflorescence.

*Season.*—May, in Monroe, Ga., Zone 7b.

*Fragrance.*—None observed.

Fruit:

*Type.*—Berry.

*Color.*—Green turning flat dark purple (RHS greyed-purple group 187A) ageing to black (RHS group 202A).

*Size.*—Round, 6.35 mm diameter.

*Season.*—Mature in September and persist into March (when they dry up), in Monroe, Ga., Zone 7b.

Disease resistance: After 12 years in field growing conditions surrounded with plants infected with leaf spot, *Entomosporium* spp., 'Corleyscourii' remained vigorous and disease free while less resistant varieties were disfigured by the unsightly leaf spot disease. In separate evaluations in nurseries in Athens, Ga., Cairo, Ga., and Houston, Tex., 'Corleyscourii' remained exceptionally free of disease, including leaf spot and fire blight, in greenhouse settings and outside in propagation areas under overhead irrigation.

I claim:

1. A new and distinct variety of *Raphiolepis×delacourii* plant, substantially as herein shown and described.

* * * * *